United States Patent [19]

Kallenbach et al.

[11] Patent Number: 5,705,723
[45] Date of Patent: Jan. 6, 1998

[54] HYDROGENATION CATALYST COMPOSITION AND A HYDROGENATION PROCESS

[75] Inventors: Lyle R. Kallenbach; Marvin M. Johnson, both of Bartlesville, Okla.

[73] Assignee: Phillips Petroleum Company, Bartlesville, Okla.

[21] Appl. No.: 547,217

[22] Filed: Oct. 24, 1995

[51] Int. Cl.[6] ............................ C07C 5/10; B01J 23/755; B01J 21/02

[52] U.S. Cl. .................. 585/270; 502/202; 502/207; 502/325; 502/327; 502/335; 502/337; 502/349

[58] Field of Search ................ 585/270, 266, 585/269; 502/202, 207, 325, 327, 335, 337, 349

[56] References Cited

U.S. PATENT DOCUMENTS

| | | | |
|---|---|---|---|
| 2,349,904 | 5/1944 | Hachmuth | 502/202 |
| 3,341,613 | 9/1967 | Hann | 260/667 |
| 3,856,702 | 12/1974 | McArthur | 252/432 |
| 4,024,171 | 5/1977 | McArthur | 260/449.6 M |
| 4,034,061 | 7/1977 | McArthur | 423/213.5 |
| 5,264,407 | 11/1993 | Satek et al. | 502/207 |
| 5,427,689 | 6/1995 | Kallenbach et al. | 210/670 |
| 5,461,021 | 10/1995 | Kallenbach | 502/202 |

OTHER PUBLICATIONS

Catalyst Data Sheets on "Nickel Spheres" and Nickel Tablets; Mallinckrodt, Inc., Calsicat Division, Erie, PA; Jan. 1985.

*Primary Examiner*—Glenn Caldarola
*Assistant Examiner*—Bekir L. Yildirim
*Attorney, Agent, or Firm*—Lucas K. Shay; Karl K. Brandes

[57] ABSTRACT

A composition comprises nickel and a support material which comprises aluminum borate and zirconium borate. In one embodiment, this composition additionally comprises rhenium. Preferably, the catalyst support material is a coprecipitate of aluminum borate and zirconium borate.

The above-described composition is employed as a catalyst for hydrogenating aromatic hydrocarbons to saturated hydrocarbons.

25 Claims, No Drawings

HYDROGENATION CATALYST COMPOSITION AND A HYDROGENATION PROCESS

BACKGROUND OF THE INVENTION

This invention relates to a novel metal borate-containing composition, which is effective as a catalyst for hydrogenating aromatic hydrocarbons.

SUMMARY OF THE INVENTION

It is an object of this invention to provide a novel metal borate-containing composition. It is another object of this invention to employ this novel composition in a process for hydrogenating aromatic hydrocarbons. Other objects will become apparent from the detailed description and the appended claims.

In accordance with this invention, a composition of matter comprises (a) nickel and (b) a support material comprising aluminum borate and zirconium borate. In one embodiment, this composition of matter further comprises (c) rhenium. In another preferred embodiment, component (b) of this composition is a coprecipitate (which has been prepared by a method comprising coprecipitation from a solution comprising at least one aluminum salt, at least one zirconium salt and at least one boric acid).

Also in accordance with this invention, in a process for catalytically hydrogenating at least one aromatic hydrocarbon containing 6–22 carbon atoms per molecule with hydrogen gas to at least one saturated hydrocarbon selected from the group consisting of alkanes and cycloalkanes, the improvement comprises employing as the catalyst the above-described composition comprising components (a) and (b), and optionally also (c).

DETAILED DESCRIPTION OF THE INVENTION

Component (a) of the composition of matter of this invention can be nickel metal, at least one nickel compound (preferably nickel oxide, NiO) or a mixture of nickel metal and nickel compound(s).

Support component (b) of the composition of this invention comprises (preferably consists essentially of) aluminum borate and zirconium borate. Generally, component (b) has a weight ratio of Al to Zr in the range of about 2:1 to about 20:1 (preferably about 4:1 to about 12:1) and a weight ratio of (Al+Zr) to B in the range of about 1:1 to about 6:1 (preferably about 1.5:1 to about 3:1). Generally, component (b) has a surface area (measured by the BET method employing $N_2$) of about 200 to about 400 $m^2$/g and a pore volume (measured by a pore size distribution method employing $N_2$) of about 0.2–1.5 cc/g. It can have any suitable shape (spherical, cylindrical, trilobal or irregular) and any suitable particle size (preferably about 0.4–0.8 mm). If particles of component (b) have been compacted and extruded, the formed cylindrical extrudates generally have a diameter of about 1–4 mm and a length of about 3–10 mm. It is within the scope of this invention to have minor amounts of aluminum oxide and zirconium oxide (generally about 1–5 weight-% of each) present in component (b).

Preferably, component (b) is prepared by a method comprising coprecipitation. First, an aqueous solution containing any water-soluble, non-hydrolyzable aluminum salt (preferably aluminum nitrate), any water-soluble, non-hydrolyzable zirconium salt (preferably zirconyl nitrate) and any water-soluble, non-hydrolyzable, acidic boron compound (preferably a boric acid, more preferably $H_3BO_3$) is prepared. Any suitable concentrations of these compounds in the aqueous solution can be employed, generally about 0.02–1 mole/l of each, depending on the desired Al:Zr:B ratio. Generally, the initial pH of this aqueous solution is about 1–3. Then an aqueous alkaline solution (preferably an aqueous solution of ammonia containing about 25–28 weight-% $NH_3$), generally having a pH of about 10–14, is added to the first aqueous solution in an amount sufficient to raise the pH of the first solution to above 7, preferably to about 8–9, so as to afford the coprecipitation of borates of aluminum and zirconium. The dispersion of the formed coprecipitate in the aqueous solution is then subjected to any suitable solid-liquid separation (preferably filtration) so as to substantially separate the coprecipitate from the aqueous solution. Preferably, the coprecipitate is washed with water (to remove adhered solution therefrom), optionally followed by washing with a water-soluble organic solvent such as methanol, ethanol, isopropanol (preferred), acetone and the like. The washed coprecipitate is generally dried (preferably in a vacuum oven at a temperature of about 110°–180° C. for about 2–16 hours) and is then calcined (generally in air, at a temperature of about 450°–550° C. for about 3–16 hours). It is within the scope of this invention to mix the formed coprecipitate with a carbon-containing binder material, such as a polyglycol, a polyoxazoline or carbon black (which is substantially burned off during the calcining step) and/or with an inorganic binder material (such as colloidal alumina, clay, calcium aluminate, water glass). It is also within the scope of this invention to extrude or pelletize or tablet the coprecipitate (with or without a binder) before the calcination.

Component (a) can be combined with component (b) in any suitable manner so as to prepare the composition of matter of this invention. Generally, component (b) is first impregnated with at least one dissolved nickel compound (such as by incipient wetness impregnation) or by spraying component (b) with an impregnating solution containing at least one dissolved nickel compound. Generally, the concentration of the at least one nickel compound in the impregnating solution is in the range of about 0.2–2 mol/l. Preferably, the solvent of the impregnating solution is water or an alcohol (such as ethanol) or mixtures thereof. Suitable Ni compounds which can be used to impregnate component (b) include (but are not limited to) nickel (II) chloride, nickel(II) nitrate, nickel(II) sulfate, ammonium nickel(II) sulfate, nickel(II) acetate, nickel(II) oxalate, hexamminenickel(II) chloride, hexamminenickel(II) nitrate, hexamminenickel(II) sulfate, and other coordination compounds of divalent nickel. Presently preferred is nickel(II) nitrate, more preferably $Ni(NO_3)_2 \cdot 6H_2O$.

If it is desired to impregnate component (b) additionally with at least one rhenium compound, this can be done before or concurrently with or after the impregnation with the at least one nickel compound. The concentration of the Re compound in the impregnating solution generally is about 0.01–1 mol/l. The solvent of this impregnating solution can be water and/or an alcohol (such as ethanol) or any other suitable liquid in which the particular Re compound is soluble and stable. Suitable rhenium compounds which can be used to impregnate component (b) include (but are not limited to) rhenium oxides (such as $Re_2O_7$), rhenic acid ($H_2ReO_4$), perrhenic acid ($HReO_4$), alkali metal rhenates (such as $Na_2ReO_4$), alkali metal perrhenates (such as $NaReO_4$), ammonium rhenate and ammonium perrhenate.

The weight ratio of the Ni-containing impregnating solution to component (b) is such as to attain a weight percentage of about 2–50 (preferably about 5–25; more preferably about 8–13) weight-% nickel (on an elemental basis) in the finished composition (i.e., the composition of matter obtained in the last step of the preparation method of this invention). If impregnation with at least one Re compound is also carried out, the weight ratio of the Re-containing impregnating solution to component (b) generally is such as to attain a weight percentage of about 0.5–10 (preferably about 2–8) weight-% Re (on an elemental basis) in the finished composition. Generally, the weight ratio of Re to Ni in the finished catalyst composition is about 0.01:1 to about 2:1 (preferably about 0.1:1 to about 1:1).

The nickel- (and optionally also rhenium-) impregnated component (b) generally is dried (preferably at a temperature of about 80°–150° C.) and then calcined at a temperature of 300°–650° C. (preferably 450°–550° C.), generally for a time period of about 0.5–20 hours (preferably about 2–4 hours). The calcining step can be done in an inert atmosphere (e.g., $N_2$, He, Ne, Ar and the like) or in an $O_2$-containing atmosphere (e.g., air).

Before its use as a hydrogenation catalyst, the obtained calcined material generally is treated with a reducing gas, preferably a gas stream which comprises (more preferably consists essentially of) free hydrogen ($H_2$), generally at a temperature of about 200°–550° C. (preferably about 350°–450° C.) for a time period of about 0.5–10 hours. Other, less preferred reducing gases include (but are not limited to) carbon monoxide, $C_1$–$C_6$ alkanes, and $C_2$–$C_6$ alkenes and $C_4$–$C_6$ alkadienes.

The composition of this invention generally contains about 2–50 (preferably about 5–25, more preferably about 8–13) weight-% Ni and about 0–10 (preferably about 0.5–10, more preferably about 2–8) weight-% Re, and has a surface area (measured by the BET method employing $N_2$) of about 200–400 m²/g.

The composition of matter is this invention (described above) can be used in a variety of catalytic applications. Preferably, the composition is employed as a catalyst for hydrogenating aromatic hydrocarbons with hydrogen gas ($H_2$) to non-aromatic hydrocarbons, such as alkenes, alkanes, cycloalkenes, cycloalkanes and the like. Suitable feed aromatic hydrocarbons which can be hydrogenated in accordance with this invention generally contain 6–22 carbon atoms per molecule and include (but are not limited to) benzene, toluene, ethylbenzene, o-xylene, m-xylene, p-xylene, trimethylbenzenes, tetramethylbenzenes, pentamethylbenzene, hexamethylbenzenes, methylethylbenzenes, ethyl-substituted benzenes, n-propyl-substituted benzenes, isopropyl-substituted benzenes, n-butyl-substituted benzenes, isobutyl-substituted benzenes, t-butyl-substituted benzenes, naphthalene, and the like, and mixtures thereof.

In a preferred application, the liquid hydrocarbon feed stream comprises at least one of the above-listed aromatic hydrocarbons as a minor component (i.e., less than about 50 weight-%, preferably about 0.1–10 weight-% of the feed) and alkanes (preferably branched) containing 8–20 (more preferably 9–18) carbon atoms per molecule) as the major portion (i.e., more than about 50 weight-%, preferably at least about 90 weight-% of the feed). A preferred feedstock has been prepared by an alkylation process, and can be used as a specialty solvent (marketed under the tradename "Soltrol® Solvent" by Phillips Chemical Company, Borger, Tex.). The presence of aromatic hydrocarbons in this type of feedstock is undesirable, and can be removed by the hydrogenation process of this invention employing the catalyst composition of this invention.

Typical hydrogenation conditions include a reaction temperature of about 150°–230° C. (preferably about 160°–200° C.), a reaction pressure of about 350–550 psig (preferably about 400–450 psig), a liquid hourly space velocity of the hydrocarbon feed stream (cc liquid feed per cc catalyst per hour) of about 1–3 cc/cc/hour (preferably about 1.5–2 cc/cc/hour), and a gas hourly space velocity of hydrogen gas of about 100–300 cc/cc catalyst/hour (preferably about 150–200 cc/cc/hour). The amount of $H_2$ gas should be sufficient to hydrogenate essentially all aromatic hydrocarbons to saturated hydrocarbons. Generally, the aromatic hydrocarbon-containing feed stream is passed, together with a $H_2$ stream, through a catalyst bed (either a fixed or a fluidized catalyst bed) containing the composition of matter of this invention as the catalyst.

The hydrogenated product which exits the hydrogenation zone can undergo any desired separation (preferably distillation) or a series of separations so as to obtain various purified product streams, primarily an alkane stream from which aromatic hydrocarbons have been substantially removed (by conversion by the hydrogenation process of this invention). The product of this hydrogenation process frequently is a mixture of alkanes and cycloalkanes, and each product component can be recovered from the hydrogenation product by suitable, effective separation means.

The following examples are presented to further illustrate the invention and are not to be considered as unduly limiting the scope of the invention.

EXAMPLE I

This example illustrates the preparation of various supported nickel catalyst compositions.

Control Catalyst A was a Ni/$Al_2O_3$ catalyst containing 54.5 weight-% nickel (provided by Engelhard Corporation, Iselin, N.J., under the "3285" product designation) which had been activated by heating in a hydrogen gas stream for 3 hours at 650° F.

Control Catalyst B was a Ni/$Al_2O_3$ catalyst containing 14.3 weight-% Ni (provided by Crossfield Company, Joliet, Ill., under the product designation "HTC400") which had been activated by heating in a hydrogen gas stream for 3 hours at 650° F.

Invention Catalyst C was Ni/Al—Zr borate containing 12.9 weight-% Ni. First, the Al—Zr borate support material was prepared as follows: 13.8 grams (0.05 mole) of ZrO($NO_3$)$_2$·$2H_2O$ (formula weight: 267) and 221 grams (0.59 mole) of Al($NO_3$)$_3$·$9H_2O$ (formula weight: 375) were mixed with 49.5 grams (0.80 mole) of $H_3BO_3$ (orthoboric acid; formula weight: 62) and 1.5 liters of distilled water. The mixture was heated and stirred until all solids were dissolved. Thereafter, concentrated aqueous ammonia was added to the entire mixture (pH: about 2) until the pH rose to about 8 and an Al—Zr-borate coprecipitate was formed. The filter cake was washed with about 1.5 liter of distilled water and then with 1.5 liter of isopropanol. The solid filter cake was dried at 150° C. overnight in a vacuum oven, followed by calcining in air at 500° C. The calcined Al—Zr borate material had a surface area (measured by the BET method using $N_2$) of 295 m²/g and a pore volume (measured by a $N_2$ pore size distribution method) of 0.36 cm³/g. It contained 30.0 weight-% Al, 8.4 weight-% Zr and 11.0 weight-% B (boron).

Then 40 grams of the Al—Zr borate support material was impregnated with a solution of 35.3 grams Ni($NO_3$)$_2$·$6H_2O$ in 100 grams of methanol. The impregnated material was dried and activated by heating in a hydrogen gas stream for 3 hours at about 343° C.

Invention Catalyst D was Ni/Re/Al—Zr borate containing 8.2 weight-% Ni and 5.2 weight-% Re. It was prepared substantially in accordance with the method for Catalyst C, except that the Al—Zr borate support had additionally been impregnated with a solution of perrhenic acid (HReO$_4$) in methanol (containing 1.3 g Re/cc solution). Catalyst D was also activated in a hydrogen gas stream 3 hours at 343° C.

EXAMPLE II

This example illustrates the use of the catalyst described in Example I in the hydrogenation of aromatic impurities contained in a heavy alkylation containing primarily C—C isoparaffins (having been produced by Phillips Chemical Company, Borger, Tex. and being marketed under the product designation "Soltrol® Solvent". This heavy alkylation feed contained about 2 weight-% aromatic hydrocarbons, primarily isopropyl- and t-butyl-substituted mononuclear aromatic hydrocarbons (such as 1,2,4,5-tetraisopropylbenzene).

A stainless steel reactor tube (inner diameter: 0.5 inch; length: 18 inches) was filled with a top layer of 15 cc alumina (as a guard bed) and 20 cc of each of the above-described catalysts. Hydrogen gas was passed through the reactor at a flow rate of 100 cc/minute, the reactor was heated to a temperature of about 400° F., and the liquid "Soltrol® Solvent" feed (containing about 2 weight-% aromatic hydrocarbons) was passed through the reactor (concurrently with the H$_2$ stream). The hydrotreated product was quantitatively analyzed by means of a UV spectrophotometer (using 1,2,4,5-isopropylbenzene as a reference API standard). Pertinent test results are summarized in Table I.

TABLE I

| Catalyst | Time on Stream (Hours) | % Conversion of Aromatics |
|---|---|---|
| A (Control) | 100 | 96.2 |
| | 150 | 94.5 |
| | 200 | 92.9 |
| | 250 | 91.2 |
| | 300 | 89.5 |
| B (Control) | 100 | 94.8 |
| | 150 | 94.0 |
| | 200 | 93.2 |
| | 250 | 92.4 |
| | 300 | 91.7 |
| C (Invention) | 100 | 99.0 |
| | 150 | 98.9 |
| | 200 | 98.8 |
| | 250 | 98.7 |
| | 300 | 98.5 |
| D (Invention) | 100 | 99.1 |
| | 150 | 98.9 |
| | 200 | 98.6 |
| | 250 | 98.4 |
| | 300 | 98.2 |

Test data in Table I clearly show the advantages of the two invention catalysts (comprising nickel and Al—Zr borate as the support) over two control catalysts (Ni on alumina): higher initial activity and considerably less rapid catalyst deactivation.

Reasonable variations, modifications and adaptations for various conditions and reactants can be made within the scope of the disclosure and the appended claims without departing from the scope of this invention.

That which is claimed:

1. A composition of matter comprising (a) nickel and (b) a support material which comprises aluminum borate and zirconium borate.

2. A composition in accordance with claim 1, wherein the weight ratio of Al to Zr in said support material is about 2:1 to about 20:1 and the weight ratio of (Al+Zr) to B in said support material is about 1:1 to about 6:1.

3. A composition in accordance with claim 1, wherein said support material is a coprecipitate of aluminum borate and zirconium borate.

4. A composition in accordance with claim 1 comprising about 2–50 weight-% nickel.

5. A composition in accordance with claim 4 comprising about 5–25 weight-% nickel.

6. A composition in accordance with claim 1 additionally comprising rhenium.

7. A composition in accordance with claim 6 comprising about 2–50 weight-% nickel and about 0.5–10 weight-% rhenium.

8. A composition in accordance with claim 7 comprising about 5–25 weight-% nickel and about 2–8 weight-% rhenium.

9. A composition in accordance with claim 7, wherein the weight ratio of rhenium to nickel is about 0.01:1 to about 2:1.

10. In a process for catalytically hydrogenating at least one aromatic hydrocarbon containing 6–22 carbon atoms per molecule with hydrogen gas to at least one saturated hydrocarbon, the improvement which comprises employing as the catalyst a composition comprising (a) nickel and (b) a support material which comprises aluminum borate and zirconium borate.

11. A process in accordance with claim 10, wherein the weight ratio of Al to Zr in said support material is about 2:1 to about 20:1 and the weight ratio of (Al+Zr) to B in said support material is about 1:1 to about 6:1.

12. A process in accordance with claim 10, wherein said support material is a coprecipitate of aluminum borate and zirconium borate.

13. A process in accordance with claim 10, wherein said catalyst comprises about 2–50 weight-% nickel.

14. A process in accordance with claim 13, wherein said catalyst comprises about 5–25 weight-% nickel.

15. A process in accordance with claim 10, wherein said catalyst additionally comprises rhenium.

16. A process in accordance with claim 15, wherein said catalyst comprises about 2–50 weight-% nickel and about 0.5–10 weight-% rhenium.

17. A process in accordance with claim 16, wherein said catalyst comprises about 5–25 weight-% nickel and about 2–8 weight-% rhenium.

18. A process in accordance with claim 16, wherein the weight ratio of rhenium to nickel in said catalyst is about 0.01:1 to about 2:1.

19. A process in accordance with claim 10, wherein said at least one aromatic hydrocarbon is contained as a minor component in a liquid hydrocarbon feed stream comprising alkanes containing 8–20 carbon atoms per molecule as the major component.

20. A process in accordance with claim 19, wherein reaction conditions comprise a reaction temperature of about 150°–230° C., a reaction pressure of about 350–550 psig, a liquid hourly space of said liquid hydrocarbon feed stream of about 1–3 cc/cc catalyst/hour, and a gas hourly space velocity of hydrogen gas of about 100–300 cc/cc catalyst/hour.

21. A composition comprising (a) nickel and (b) a support material which comprises aluminum borate and zirconium borate wherein the weight ratio of Al to Zr in said support material is about 2:1 to about 20:1 and the weight ratio of (Al+Zr) to B in said support material is about 1:1 to about 6:1; and said composition comprises about 2 to about 50 weight % nickel.

22. A composition in accordance with claim 21, wherein the weight ratio of Al to Zr in said support material is about 4:1 to about 12:1; the weight ratio of (Al+Zr) to B in said support material is about 15:1 to about 3:1; and said composition comprises about 2 to about 25 weight % nickel.

23. A composition in accordance with claim 21 additionally comprising rhenium.

24. A composition in accordance with claim 23 comprising about 0.5 to about 10 weight % rhenium.

25. A composition in accordance with claim 24 comprising about 2 to about 8 weight % rhenium.

* * * * *